United States Patent [19]
Coss

[11] Patent Number: 5,096,418
[45] Date of Patent: Mar. 17, 1992

[54] MOTORIZED DENTAL HANDPIECE WITH FIBER OPTIC ILLUMINATION

[75] Inventor: Ronald G. Coss, Newport Beach, Calif.

[73] Assignee: Micro Motors, Inc., Santa Ana, Calif.

[21] Appl. No.: 547,966

[22] Filed: Jul. 5, 1990

[51] Int. Cl.$^5$ .......................... A61C 1/00; A61C 3/00; A61C 1/05

[52] U.S. Cl. ...................................... 433/29; 433/115

[58] Field of Search ................. 433/29, 103, 114, 115, 433/131, 132

[56] References Cited

U.S. PATENT DOCUMENTS

| | | | |
|---|---|---|---|
| 3,309,965 | 3/1967 | Weickgenannt | 433/132 |
| 3,439,422 | 4/1969 | Doeden | 433/132 |
| 3,634,938 | 1/1972 | Hutchinson | 433/29 |
| 3,683,503 | 8/1972 | Klein | 433/29 |
| 3,758,951 | 9/1973 | Scrivo et al. | 433/29 |
| 3,789,506 | 2/1974 | Johns | 433/29 |
| 3,893,134 | 7/1975 | Lieb ete al. | 354/436 |
| 3,897,134 | 7/1975 | Scrivo et al. | 350/96.22 |
| 4,014,098 | 3/1977 | Scrivo et al. | 433/29 |
| 4,020,556 | 5/1977 | Sotman | 433/29 |
| 4,341,518 | 7/1982 | Wallace | 433/29 |
| 4,477,252 | 10/1984 | Lieb et al. | 433/29 |
| 4,568,284 | 2/1986 | Stankiewicz | 433/126 |
| 4,578,033 | 3/1986 | Mossle et al. | 433/29 |
| 4,578,034 | 3/1986 | Shibata et al. | 433/29 |
| 4,600,384 | 7/1986 | Olsen | 433/29 |
| 4,642,738 | 2/1987 | Meller | 362/119 |
| 4,648,838 | 3/1987 | Schlachter | 433/29 |
| 4,669,982 | 6/1987 | Fleer | 433/29 |
| 4,790,751 | 12/1988 | Reinhardt et al. | 433/29 |

Primary Examiner—John J. Wilson
Assistant Examiner—C. A. Cherichetti
Attorney, Agent, or Firm—Knobbe, Martens, Olson & Bear

[57] ABSTRACT

An air motor and accompanying air distributor and motor output drive means are axially stacked within a tubular dental handpiece. A fiber optic bundle extends through a special passage in the thick-wall side of an eccentrically positioned cavity in the motor casing. The bundle also extends axially through the other components in the handpiece and further is directed to a dental tool head mounted on one end of the handpiece. The fiber optic bundle very effectively illuminates a cutting burr or other element mounted on the tool head, a gasket adjacent the motor prevents leakage of air past the metal-to-metal surfaces of the air motor and surrounding housing. The gasket is also provided with a hole through a thick-edge wall for the fiber optic bundle. A further flat resilient seal prevents air passage passed the motor output shaft and the spaces between the bearing races.

7 Claims, 3 Drawing Sheets

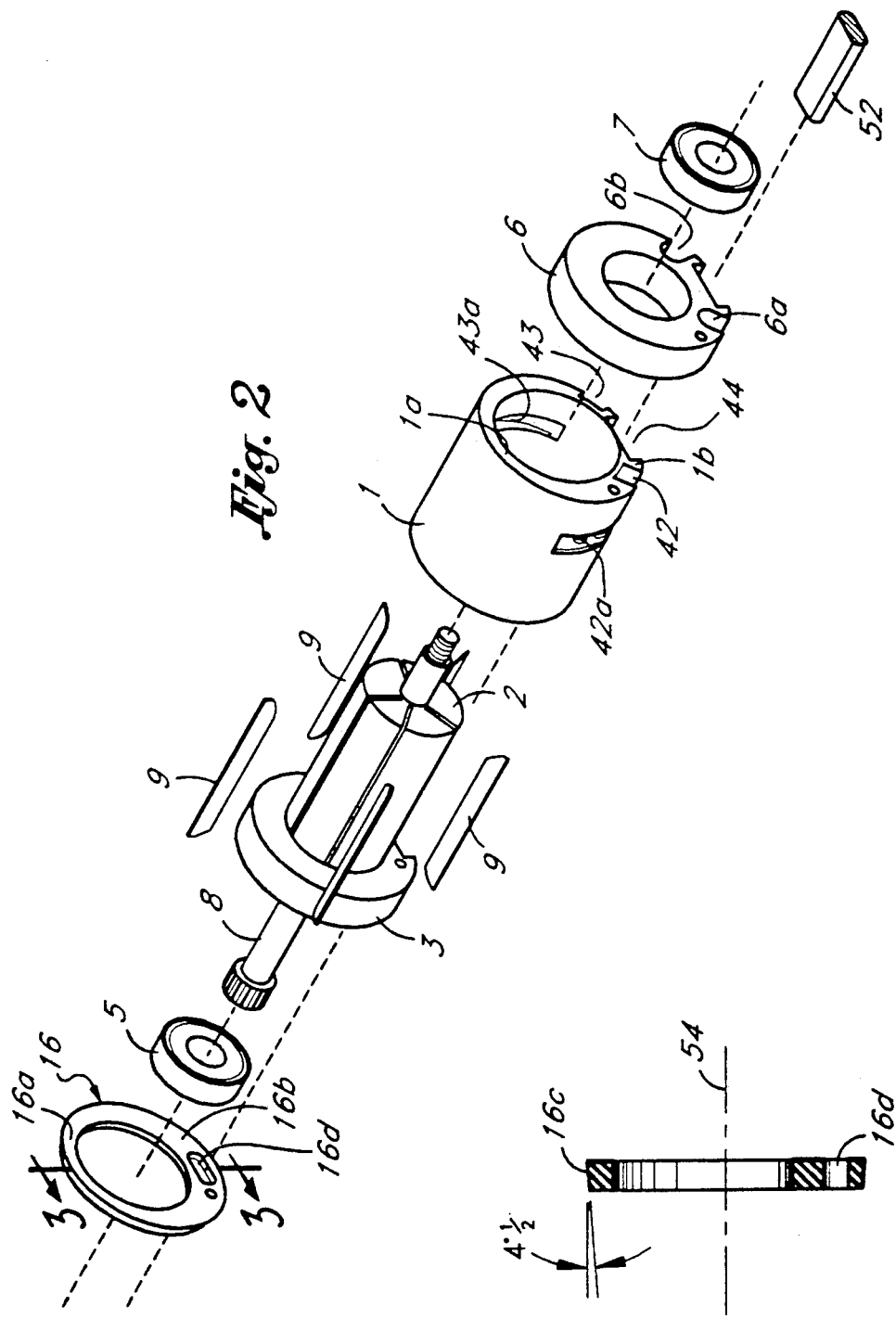

MOTORIZED DENTAL HANDPIECE WITH FIBER OPTIC ILLUMINATION

BACKGROUND OF THE INVENTION

This invention is related to an improved illumination system for a motorized dental handpiece. Motorized dental handpieces, of course, require an adequate light source at the tip to enable the dentist to properly view the area to which the tool is being applied. The advent of fiber optics for transmitting light has provided an advance in dental tool illumination systems.

For high speed bur driving turbines mounted on the tip of a handpiece, there have been a number of systems developed using fiber optics. Also, U.S. Pat. No. 3,634,938 discloses a handpiece wherein the fiber bundle is simply mounted on the exterior of an existing handpiece. Several U.S. patents show high speed turbine tip dental handpieces with the bundle within the handpiece. However, low speed devices having the motor in the handpieces present a greater challenge for utilizing fiber optic illumination.

One goal in the design of motorized dental handpieces is to minimize weight so as to minimize hand fatigue and to facilitate handling and maneuverability of the handpiece. It is also a goal to minimize the diameter of the handpiece, as well as its length in that these factors also affect fatigue and maneuverability. Positioning a fiber optic bundle either in the wall of the handpiece housing or in between the housing and the exterior of the motor normally positioned within the housing, tends to make the units bulkier than desired or, one unit on the market, utilizes a smaller motor to avoid bulk, but this sacrifices power.

With an air-driven motor mounted in the handle, air leakage downstream can occur around the fiber optic bundle. This is undesirable in that the leaked air can blow debris around the working area, which impairs the dentist's view and irritates the patient's sinus. Also, since the leaked air can be 20 to 30% of the volume applied to the motor, there is a resulting power loss.

One solution to this problem has been to position epoxy between the fiber optic bundle and the surrounding structure in the handle. While this is effective, it is not very satisfactory in that to service the product, the epoxy seal is broken and a new seal material must be applied and set after the servicing is completed. This is bothersome and time consuming. Further, the fiber optic bundle is usually damaged during breaking the seal, and thus must then be replaced, adding further delay and expense.

U.S. Pat. No. 4,568,284 employs a drive shaft driven by a turbine in a handle with a light source and fiber bundle between the motor and the driven bur. Since the motor can be easily sealed without the optic bundle, this avoids the air leakage problem but has other difficulties.

Accordingly, a need exists for a dental handpiece having a handle mounted motor with an improved fiber optic illumination system.

SUMMARY OF THE INVENTION

In accordance with the present invention, a known dental handpiece has been uniquely modified to accommodate a fiber optic light assembly without increasing the diameter of the handpiece, so that the unit remains conveniently sized. The handpiece includes an air-driven sliding vane-type motor which has an outer cylinder positioned immediately within a surrounding housing. A cylindrical cavity is formed within the cylinder with the center line of the cavity being eccentric with respect to the center line of the cylinder and the surrounding housing. This creates a cylinder wall which varies from a thin radial dimension on one side of the housing to a thicker opposite side. A passage is formed in the thick wall, extending generally parallel to the axis of the housing. A fiber optic bundle is installed through this passage with the result that fiber optic illumination is provided without increasing the size of the unit.

To prevent air leakage from being transmitted downstream to the tool end of the handpiece, there is provided a gasket on the downstream side of the motor downstream end plate. The outer edge of the gasket is adapted to prevent leakage between the gasket and the surrounding housing, and between the gasket and the adjacent end plate. The gasket is also formed with an opening through which the fiber optic bundle extends, and the opening is sized to prevent leakage around the fiber optic bundle. All of the components are axially compressed within the housing so that the gasket is compressed against the downstream end plate and an adjacent motor spacer or other structure.

SUMMARY OF THE DRAWINGS

FIG. 2 is an exploded perspective view of the motor and gasket portion of FIG. 1.

FIG. 3 is a cross-sectional view of the gasket of FIG. 2 on line 3—3.

DETAILED DESCRIPTION OF THE PREFERRED EMBODIMENT

Figure 1:
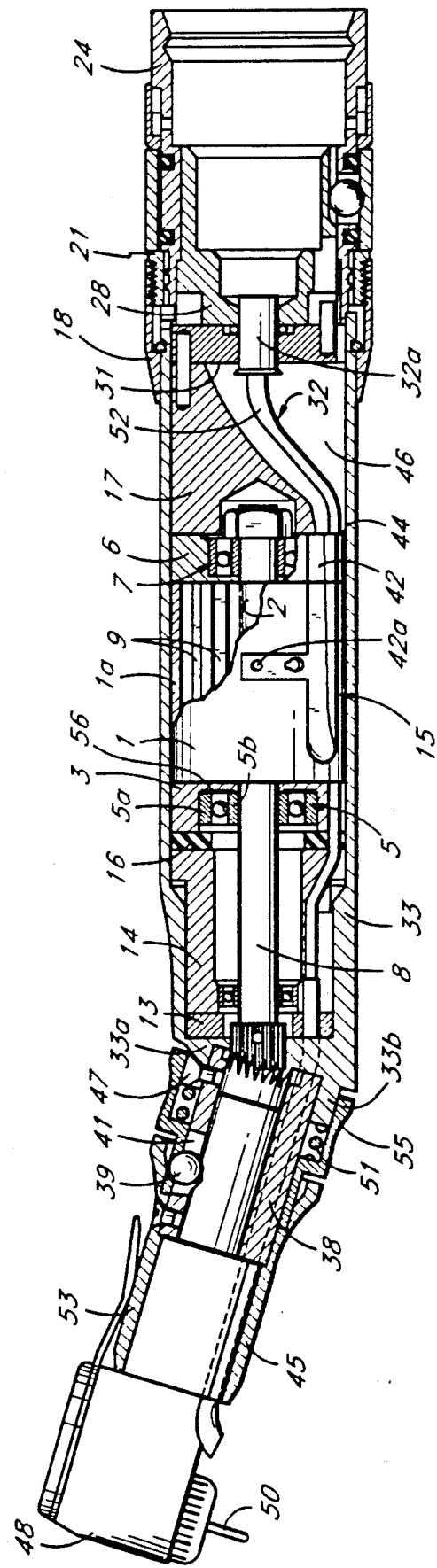
FIG. 1 is a longitudinal cross section of a motorized dental handpiece.

Referring to FIGS. 1 and 2, there is illustrated an elongated, motorized dental handpiece including an outer housing 33 having a cylindrical exterior and a cylindrical interior bore. The forward end of the housing includes an end wall 33a having an axial opening through which an output shaft 8 extends for connection to a tool to be operated by the motorized handpiece. A series of components are stacked into the housing 33, the components being introduced through an open upper or right end of the housing. Engaging the end wall 33a within the housing is a support washer 13, followed by a tubular motor spacer 14, an annular air seal gasket 16 and an air motor 15.

The air motor includes a lower disk shaped, annular end plate 3 and a similar disk shaped, annular, upper end plate 6. Positioned between these end plates is a tubular casing or cylinder 1 having an eccentrically positioned interior cylindrical cavity in which is positioned a rotor 2. The rotor output shaft 8 is mounted in bearings 5 and 7, each of which is respectively mounted within the lower-end plate 3 and the upper-end plate 6. Upstream of the end plate is an air distributor 17, a guide plate 31, a reversing valve 28 and a swivel head 24.

The rotor 2 includes a plurality of radially oriented, axially extending pockets or slots, with each slot having a rotor blade 9 positioned in it. These blades or vanes 9 reciprocate radially in the slots, being urged outwardly by centrifugal force and inwardly by the cylinder wall. The vanes provide reacting surfaces for air introduced to the compartments formed by the blades, the rotor and the casing wall. Sliding vane motors of this general type have been utilized in dental handpieces for many years. Air for driving the rotor is introduced to the motor by way of the distributor 17 which has passages (not shown) that are aligned with and open to an inlet 6a and an outlet 6b in the upper-end plate 6 for the introduction and exhaust, respectively, of air to and from the compartments within the motor 15.

The motor housing 33 has a cylindrical exterior and a cylindrical interior with a relatively thin wall so as to keep the overall diameter of the handpiece to a minimum. Within the housing is positioned the motor casing 1, which has a cylindrical exterior that fits snugly within the surrounding housing. Since the center of the cylindrical cavity is eccentrically positioned with respect to the exterior of the casing and with respect to the housing, there is created a thin-wall portion 1a on one side, as shown in FIG. 2, and a thick-wall portion 1b on the other side of the casing. Within the thick-wall portion there is positioned an air inlet axially extending passage 42 leading to radial passage 42a, opening to the compartments formed by the rotor blades. Also formed in the thick wall portion 1b is an axially extending outlet passage 43 opening from circumferential slot 43a.

Also, there is an elongated passage 44 that extends axially through the exterior of the thick-wall portion of the casing, and likewise extends through the upper-end plate 6, the lower-end plate 3 and the gasket 16. Further, the distributor 17 has a radially extending passage 46 that opens to the motor passage 44. The passage 44 is between the air passages 42 and 43 and between inlet and outlet passages 6a and 6b.

Within this extended passage 44, 46 is positioned a fiber-optic assembly 32. That assembly has an enlarged input end 32a positioned within the reversing valve 28 and the guide plate 31. A known supply hose (not shown) fits within the swivel head 24 and supplies high pressure air to the motor, and high intensity light to the fiber optic bundle. The fiber-optic bundle 52 of that assembly 32 extends radially and axially through the distributor passage 46, and into the passage 44 in the thick-wall side of the upper-end plate 6, the cylinder or casing 1, the lower-end plate 3, and the gasket 16. The fiber bundle 52 extends further through the motor spacer 14, the support washer 13, and through the nosepiece 38, the retainer 39 and into the tool head 48. The output end of the fiber-optic assembly extends through a wall of this tool head 44, and directs its light output onto the rotating bur 50.

The use of the fiber-optic assembly greatly enhances illumination at the tool tip. However, it is necessary to prevent air leakage out of the motor cavities within the casing 1 to the tool end. The gasket 16 which prevents this leakage has a number of critical features that create the necessary sealing.

From FIG. 2, it may be seen that the gasket 16, has a circular exterior and also has a circular hole formed therein, with the center of the hole being eccentrically positioned with respect to the center of the gasket. This creates a radially thinner gasket wall portion 16a on one side and a radially thicker wall portion 16b on the other side. This thicker wall section provides sufficient area for forming a circumferentially extending elongated slot 52 or hole, which becomes a part of the passage 44, through which the fiber-optic bundle can extend in snug relation with the gasket to minimize air leakage in that area. The exterior of the gasket has an edge 16c that tapers from a smaller diameter on the forward edge to a larger diameter on the trailing edge near the motor. It can be seen that the gasket has a thin, flat configuration. The exterior of the small diameter end of the gasket is slightly smaller than the surrounding house to facilitate the insertion of the gasket into the housing. The outer diameter of the trailing edge is slightly larger than the inner diameter of the housing such that the trailing edge is pressed into sealing engagement as it is inserted into the housing. In a production version of one form of the gasket the smaller diameter is 0.005" less than the housing inner diameter, and the larger diameter is 0.005" greater. With the thin gasket selected, this creates a tapered angle of about $4\frac{1}{2}°$ with respect to a line parallel to the gasket axis 54. Thus, the gasket prevents air leakage between the lower-end plate 3 and the surrounding housing. Also, the gasket prevents leakage around the periphery of the fiber-optic bundle because the gasket material fits snugly with the fiber-optic bundle. The gasket 16 is preferably made of a compressible material such as neoprene so that the compressing action further enhances the seal against the lower-end plate and the surrounding housing.

In addition, there is a thin, flat gasket 56 located between the lower-end bearing 5 and the inner flat wall of the lower-end plate 3 to prevent leakage through the bearing races. The outer race 5a fits into the lower-end plate so that little or no leakage occurs between its periphery and the lower-end plate. Also, the inner race 5b is snugly fit onto the output shaft 8 so there is little or no air loss in that area.

In assembly, the components are stacked as illustrated in FIG. 1, and they are compressed in that position by means of the nut 18 which threads onto an adapter ring 21, which in turn is threaded onto the swivel head 24. The swivel head has an inner flange which engages an outer flange of the reversing valve 28 such that axial movement of the swivel head to the left, as viewed in FIG. 1, urges the reversing valve in that direction, compressing it against the guide plate 31. The guide plate is pressed against the distributor which engages the air motor 15, which in turn compresses the gasket 16 against the motor spacer 14 engaging the support washer 13.

Thus it can be seen that a fiber-optic lighting arrangement is provided in a dental handpiece without enlarging the diameter or appreciably affecting the weight of the unit over the existing handpiece of this type.

Figure 4:
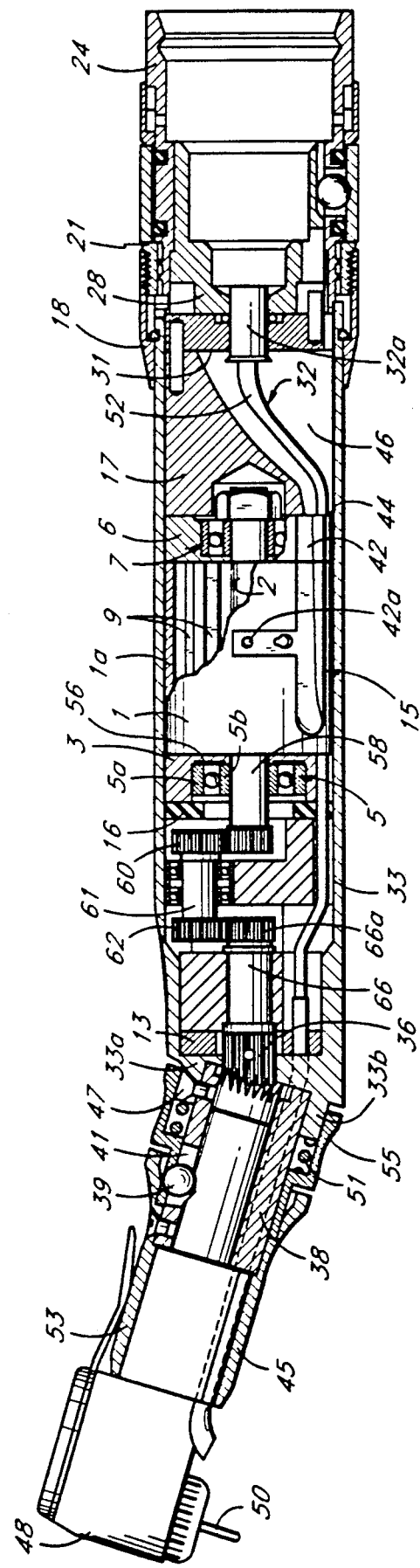
FIG. 4 is a cross-sectional view of a form of the handpiece of FIG. 1, modified to provide speed reduction gearing.

The unit illustrated in FIG. 1 has an air motor that provides a direct drive from the motor to the tool to be driven by the motor. However, in some applications lower speed is desired. This variation is illustrated in FIG. 4, wherein an output shaft 58 from the motor 15 is connected to a speed reduction arrangement including a gear 60 and a bearing-mounted stub shaft 61. Gear teeth 62 on the exterior of the shaft 61 drive a gear 66a pinned to an output shaft 66, positioned to provide power to the operating tool 50. A gasket 16 is employed to provide the necessary sealing, and the components are compressed into the housing in a manner similar to that described above.

Extending in the forward direction from the housing end wall 33a is a tubular socket 33b, which is oriented at an angle with respect to the main housing body. The lower end of the tubular nosepiece 38 is positioned within this socket and secured thereto by a suitable screw 47. A detent ball 39 is captured in a slot 41 in the wall of the nosepiece by a release ring 55 which surrounds the housing socket wall 33b as well as a major portion of the nosepiece 38. A compression spring 51 surrounds a portion of the nosepiece and extends between the end of the housing socket 33b and a flange on the release ring. The diameter of the detent ball is larger than the thickness of the nosepiece wall such that a portion extends outwardly through a hole in the release ring. This relationship causes the spring and the release ring to urge the detent ball forwardly. At the same time, the ball retains the release ring on the nosepiece. A portion of the ball also extends inwardly beyond the inner diameter of the nosepiece wall to mate with a detent recess in the periphery of a mounting shaft on the end of a tool head. The tool head shaft can be inserted into the nosepiece by pushing the detent ball radially outwardly and rearwardly against the urging of the spring. When the shaft is installed the detent recess on the shaft is aligned with the ball and the retaining ring spring urges the ring forwardly pushing the ball into the detent recess. The tool head is thereby locked to the housing.

Surrounding the forward portion of the nosepiece including the detent ball, is a tubular retainer 45, which is fastened to the nosepiece. A cylindrical portion of the tool head fits within this retainer and forms a stabilizing surface for a positioning spring 53 which is attached to the tool head and engages the exterior of the retainer. The tool head includes a mounting socket for conventionally mounting a tool 50 that extends radially outwardly from the axis of the main portion of the tool head. Rotation is transmitted to the tool by means of a gear coupler 36 which is connected to the output end of the shaft 40. This gear coupler is drivingly engaged with a drive shaft (not shown) within the head 48. Rotation of that drive shaft is transmitted by a suitable gear (not shown).

What is claimed is:

1. A motorized dental handpiece, comprising:
   an elongated housing to be held within a person's hand, said housing having a cylindrical interior;
   an air-driven motor in said housing, including a casing having a cylindrical exterior with the casing being concentrically positioned within said housing, an eccentrically formed cylindrical cavity within said casing creating a thick wall casing portion and a thin wall casing portion, a vane rotor motor mounted in said cavity with the axis of the rotor being concentric with the axis of said casing cavity, an upper end plate closing one end of said cavity and a lower end plate closing the other end of said cavity, said rotor including a shaft extending through each of said end plates, said shaft being adapted to drive a tool in the downstream end of said housing, bearings mounted in said end plate supporting said shaft, a passage through the thick wall portion of said casing and through said end plates, a rotor air inlet through said casing thick wall portion circumferentially spaced from said passage and a rotor air outlet through said casing thick wall portion circumferentially spaced from said passage, with the outlet and the inlet being on opposite sides of said passage;
   an air distributor positioned adjacent to said upper end plate for distributing air into and out of said compartments between said rotor and said casing, said upper end plate having air conduits formed therethrough opened to said air inlet and outlet;
   a fiber optic assembly extending through said distributor and to said passage in said end walls and said casing said assembly being generally elliptical in cross-sectional shape, with the longer dimensions of said shape extending circumferentially with respect to said housing; and
   a compressible gasket positioned snugly within said housing adjacent said lower end plate, said gasket being adapted to prevent or minimize air from leaking out of said cavity and between said lower end plate and said bearing, said gasket having an opening aligned with said passage, said opening being generally elliptical in shape with the longer dimension of said opening extending generally circumferentially with respect to the outer periphery of said gasket, said fiber optic assembly extending through said gasket opening in sealing relation with the gasket, said gasket having a hole through which said shaft extends with the gasket material being spaced from the shaft.

2. The apparatus of claim 1, wherein said gasket has a generally flat configuration with an eccentrically formed hole therethrough resulting in one side of said gasket being radially thick and the opposite side being radially thin, said opening for the fiber optic bundle in said gasket extends through said thick portion.

3. A motorized dental handpiece, comprising:
   an elongated housing to be held within a person's hand, said housing having a cylindrical interior;
   an air-driven motor in said housing, including a casing having a cylindrical exterior with the casing being concentrically positioned within said housing, an eccentrically formed cylindrical cavity within said casing, a vane rotor mounted in said cavity with the axis of said rotor being concentric with the axis of said cavity, an upper end plate closing one end of said cavity and a lower end plate closing the other end of said cavity, said rotor including a shaft extending through each of said end plates, said shaft being adapted to drive a tool in the downstream end of said housing, bearings mounted in said end plate supporting said shaft, a passage through a thick wall portion of said casing and through said end plate;
   an air distributor positioned adjacent to said upper end plate for distributing air into and out of compartments between said rotor and said casing, said upper end plate having air conduits formed therethrough;
   a fiber optic assembly extending through said distributor and through said passage in said end walls and said casing; and
   a gasket positioned snugly within said housing adjacent said lower end plate, said gasket being adapted to prevent or minimize air from leaking out of said cavity and between said lower end plate and said housing, said gasket having an opening aligned with said passage, said fiber optic assembly extending through said gasket opening in sealing relation with the gasket having a generally flat configuration with an eccentrically formed hole therethrough resulting in one side of said gasket being radially thick and the opposite side being radially thin, said opening for the fiber optic bundle in said gasket extending through said thick side, said opening being generally elliptical in shape with the longer dimensions of said elliptical shape extending generally perpendicular to a radial line through said gasket.

4. The apparatus of claim 3, wherein said gasket has an outer edge which is tapered from a diameter on its leading end which is smaller than the interior diameter of said housing to a larger diameter on its trailing end which is larger than the housing interior diameter.

5. A motorized dental handpiece, comprising:
an elongated housing to be held within a person's hand, said housing having a cylindrical interior;
an air-driven motor in said housing, including a casing having a cylindrical exterior with the casing being concentrically positioned within said housing, an eccentrically formed cylindrical cavity within said casing, a vane rotor mounted in said cavity with the axis of said rotor being concentric with the axis of said cavity, an upper end plate closing one end of said cavity and a lower end plate closing the other end of said cavity, said rotor including a shaft extending through each of said end plates, said shaft being adapted to drive a tool in the downstream end of said housing, bearings mounted in said end plate supporting said shaft, a passage through a thick wall portion of said casing and through said end plate;
an air distributor positioned adjacent to said upper end plate for distributing air into and out of compartments between said rotor and said casing, said upper end plate having air conduits formed therethrough;
a fiber optic assembly extending through said distributor and through said passage in said end walls and said casing; and
a gasket positioned snugly within said housing adjacent said lower end plate, said gasket being adapted to prevent or minimize air from leaking out of said cavity and between said lower end plate and said housing, said gasket having an opening aligned with said passage, said fiber optic assembly extending through said gasket opening in sealing relation with the gasket, said gasket edge tapering axially at an angle of about 5° with respect to a line parallel to the axis of said gasket.

6. The apparatus of claim 5, wherein said gasket has an outer edge which is tapered from a smaller diameter away from said lower end wall to a larger diameter adjacent said lower end wall.

7. A motorized dental handpiece, comprising:
an elongated housing to be held within the dentist's hand, said housing having an end wall;
an air-driven motor in said housing, including a cylinder wall with an eccentrically formed cylindrical cavity within said cylinder wall, a vane rotor mounted in said cavity with the axis of said rotor being concentric with the axis of said cavity, said rotor including a drive shaft extending axially from said motor and through said end wall, said motor further including an end plate adjacent said rotor, a bearing mounted in said end plate, with said bearing rotatably supporting said shaft, said bearing being sealed from said motor;
a tool connected to be rotated by said shaft;
a passage through the thicker wall of said cylinder;
an air distributor positioned adjacent said motor on the side of said rotor opposite from said end wall for distributing air into and out of spaces between the rotor and said cylinder;
a fiber optic assembly extending through the passage in said distributor, through the passage in said cylinder, and through a passage in said end plate, said assembly having a cross-sectional shape which is generally elliptical; and
a compressible gasket between said end plate and said end wall, the gasket tightly engaging the interior wall of the housing and tightly engaging said end plate to form a good air seal between the gasket and the housing, and a good air seal between the gasket and the end plate, said gasket having an inner edge spaced from said shaft, said gasket having an opening aligned with said passage, the opening having a generally elliptical shape aligned with said fiber optic assembly, said fiber optic assembly extending through said gasket opening in sealing relation with the gasket, said gasket being adapted to prevent air leakage from said cavity to said tool.

* * * * *